(12) United States Patent
Levin

(10) Patent No.: US 6,939,288 B1
(45) Date of Patent: Sep. 6, 2005

(54) AUDITORY THERAPY SYSTEM FOR IMPACTING THE NERVOUS SYSTEM OF A LIVING ORGANISM

(76) Inventor: Yakov I. Levin, Oliwpysky prospect d 30, kv. 30, Moscow 129272 (RU)

( * ) Notice: Subject to any disclaimer, the term of this patent is extended or adjusted under 35 U.S.C. 154(b) by 0 days.

(21) Appl. No.: 09/308,913
(22) PCT Filed: Dec. 26, 1996
(86) PCT No.: PCT/RU96/00364

§ 371 (c)(1),
(2), (4) Date: May 26, 1999

(87) PCT Pub. No.: WO98/19601

PCT Pub. Date: Mar. 14, 1998

(51) Int. Cl.[7] .............................................. A61B 5/0432
(52) U.S. Cl. ........................................................ 600/28
(58) Field of Search .............................. 600/26, 27, 28

(56) References Cited

U.S. PATENT DOCUMENTS 5,267,942 A * 12/1993 Saperston .................... 600/28
5,356,368 A * 10/1994 Monroe ....................... 600/28

* cited by examiner

Primary Examiner—George R. Evanisko
Assistant Examiner—Frances P. Oropeza
(74) Attorney, Agent, or Firm—I. Zborovsky

(57) ABSTRACT

A method of influencing the body has the steps of registering physical parameter biopotentials, transforming and processing of obtained data to calculate a biosignal characteristic generalized parameter, transforming the biosignal characteristic generalized parameter on the basis of detected criterial correspondence into a control signal and forming an external sound effect, implementing the external sound effect in the form of generation of musical sounds by a parametric variation tone, volume and duration thereof in criterial relation to variation of discrete current values of the characteristic generalized parameter of a frequency spectrum of the transformed biosignal.

2 Claims, 2 Drawing Sheets

AUDITORY THERAPY SYSTEM FOR IMPACTING THE NERVOUS SYSTEM OF A LIVING ORGANISM

BACKGROUND OF THE INVENTION

The invention relates to the area of medicine and may be used for bioadaptive correction of man's functional condition.

Known from the level of technology are methods of influencing the body by biological feedback, where biopotentials, mainly of brain electrical activity are recorded, transformed and the obtained electroencephalogram (EEG) is processed to isolate, from the spectrum, a certain frequency band that corresponds to alpha-rhythm, and then a control signal is formed generating sound effect on the body with the level proportional to alpha-rhythm in the EEG spectrum (see USSR Authorship Certificate No. 1124922, class A 61 B May 4, 1998; USSR Authorship Certificate No. 1780716, class A 61 B May 4, 1992; U.S. Pat. No. 3,896,790, class A 61 B May 4, 1975).

Psychophysiological effect on man in the above methods, however, is limited by control of alpha activity which does not allow to effectively correct functional condition of the body.

Also known is the method of body functional condition correction with optimization of parameters of external effect on the body which includes recording of physiological parameter biopotentials, transformation and processing of the obtained information with calculation of a biosignal characteristic parameter which is transformed into a control signal, and external effect signals are formed on the basis of the data obtained (see USSR Authorship Certificate No. 1745204, class A 61 B May 4, 1992).

In this case the external effect, e.g. background sound, is selected from various prerecorded phonograms that differ in volume, rhythm, and tone, using biological feedback to optimize deviation of current characteristic value of the selected biosignal registered during correction of patient's functional condition from the estimated one determined in the preparatory mode. These prerecorded phonograms, however, are of random nature and may not fully correspond to individual features of the body, which reduces effectiveness of man's physiological condition psychophysiological correction by external effect of physical factors, e.g. sound.

SUMMARY OF THE INVENTION

The invention is aimed at creation of a method to influence the body by means of external physical factor—a sound in the form of a musical tune that adequately reflects man's psychophysiological condition.

Solution of the problem is provided by that the method of influencing the body which includes registration of physiological parameter biopotentials, transformation and processing of the obtained data with calculation of biosignal characteristic generalized parameter, which on the basis of detected criterial correspondence is transformed into a control signal and signals of external sound effect are formed, according to the invention, external sound effect is implemented as generation of musical sounds by parametric variation of their tone, volume, and duration in criterial dependence of variation of value of discrete current generalized parameter of transformed biosignal frequency spectrum, thus from the recorded graphic data isolated are time intervals of identical duration, which are transformed, using the Fourier harmonic analysis, into a frequency spectrum, then a generalized characteristic dimensionless parameter is determined for each spectral interval, a proportional range of musical sound parameters is formed between minimum and maximum values of the generalized dimensionless parameter, appropriate values of sound tone, volume, and duration are determined for each spectral interval by numerical value of its generalized dimensionless parameter, which are then transformed by a synthesizer into sound signals formed in a sequence that corresponds to initially recorded discrete current alternation of time intervals.

The generalized dimensionless parameter is determined by ratio of power spectral density of at least two characteristic frequency bands isolated in each spectral interval.

A positive outcome of the claimed method is primarily provided by that sound reproduction of physiological activity biosignals is based on the analogy of oscillatory nature of recorded biosignal variation (electroencephalogram—EEG, electrocardiogram—ECG, electrogastrogram—EGG, electromyogram, electroretinogram, pulse wave oscillogram, etc.) and sound oscillatory nature, while suggested criterial dependence between characteristic generalized parameter of frequency spectrum of transformed biosignal and parameters of generated musical sound (tone, volume, and duration) most adequately reflects individual features of man's functional condition and allows to form sequence of sounds in the form of personality music which, if recorded in magnetic medium while the patient is in healthy condition, allows to effectively correct depressive conditions, sleep disturbance, anxiety and other psychophysiological disorders by music therapy.

DESCRIPTION OF THE PREFERRED EMBODIMENTS

The method suggested is implemented as follows.

Preliminary, during a satisfactory period of patient's healthy condition, physiological parameter biopotentials, e.g. bioelectric activity of brain, heart muscles, stomach, skeletal muscles, eye retina, pulse waves, etc., are recorded using well-known advanced instrumentation.

Electroencephalogram, EEG, is the most universal and adequately reflects individual functional condition; an example of EEG transformation into the "brain music" is given below.

Figure 1:
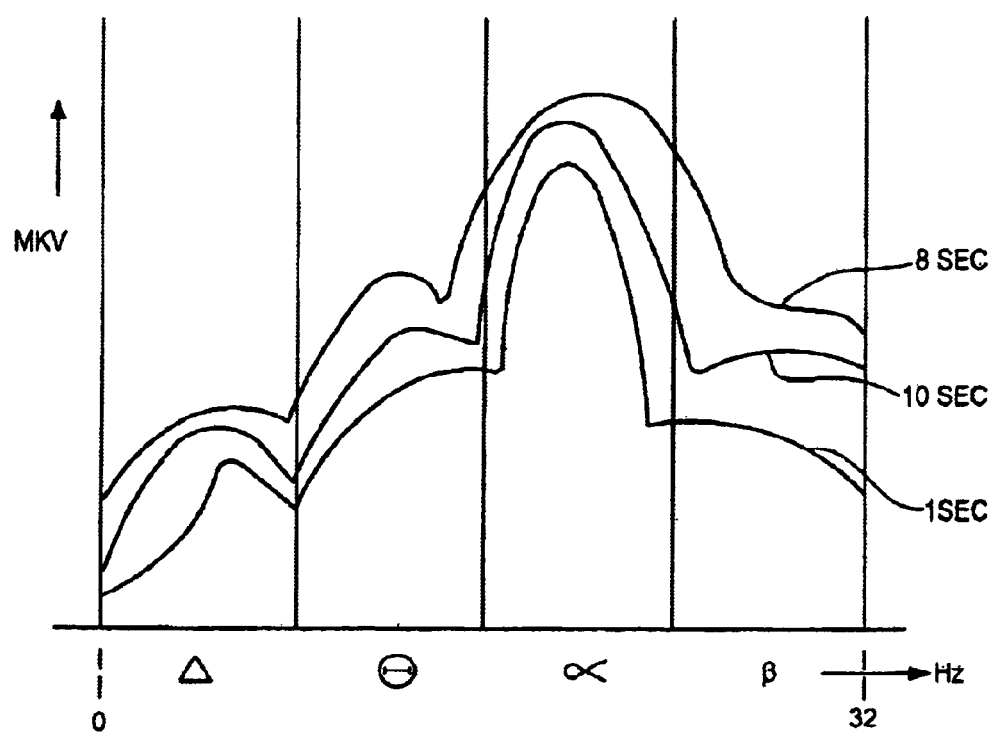
FIG. 1 shows the set of frequency spectra with discrete current alternation of time intervals.

EEG registered, e.g. within 10 seconds, is divided into equal time intervals of, e.g. 1 second duration; using harmonic analysis, a Fourier expansion, each interval is transformed into frequency spectrum (see FIG. 1), 4 common frequent ranges ($\Delta$, $\theta$, $\alpha$, $\beta$) are isolated pursuant to the international standard:

$\Delta$=0.1–3.9 Hz, $\Theta$=4.0–7.9 Hz, $\alpha$=8.0–12.9 Hz, $\beta$=13.0–32.0 Hz, and a dimensionless generalized characteristic parameter is determined for each spectral interval with respect to power spectral densities $\Theta$ and $\beta$ intervals, namely:

$K_1 = P_1\Theta/P_1\beta = 15.0/30.0 = 0.5$ (for 1st second)
$K_2 = P_2\Theta/P_2\beta = 42.0/20.0 = 2.1$ (for 2nd second)
$K_3 = P_3\Theta/P_3\beta = 54.0/12.0 = 4.5$ (for 3rd second)
$K_4 = P_4\Theta/P_4\beta = 76.0/20.0 = 3.8$ (for 4th second)
$K_5 = P_5\Theta/P_5\beta = 81.4/11.0 = 7.4$ (for 5th second)
$K_6 = P_6\Theta/P_6\beta = 105.0/10.0 = 10.5$ (for 6th second)
$K_7 = P_7\Theta/P_7\beta = 78.4/93 = 0.8$ (for 7th second)
$K_8 = P_8\Theta/P_8\beta = 101.8/5.5 = 18.5$ (for 8th second)
$K_9 = P_9\Theta/P_9\beta = 51.0/8.5 = 6.0$ (for 9th second)
$K_{10} = P_{10}\Theta/P_{10}\beta = 135.0/6.0 = 12.5$ (for 10th second), where K—dimensionless generalized parameter;

$P\Theta$, $P\beta$—spectral density of characteristic frequency band power (sq$\mu$V\sec).

Figure 2:
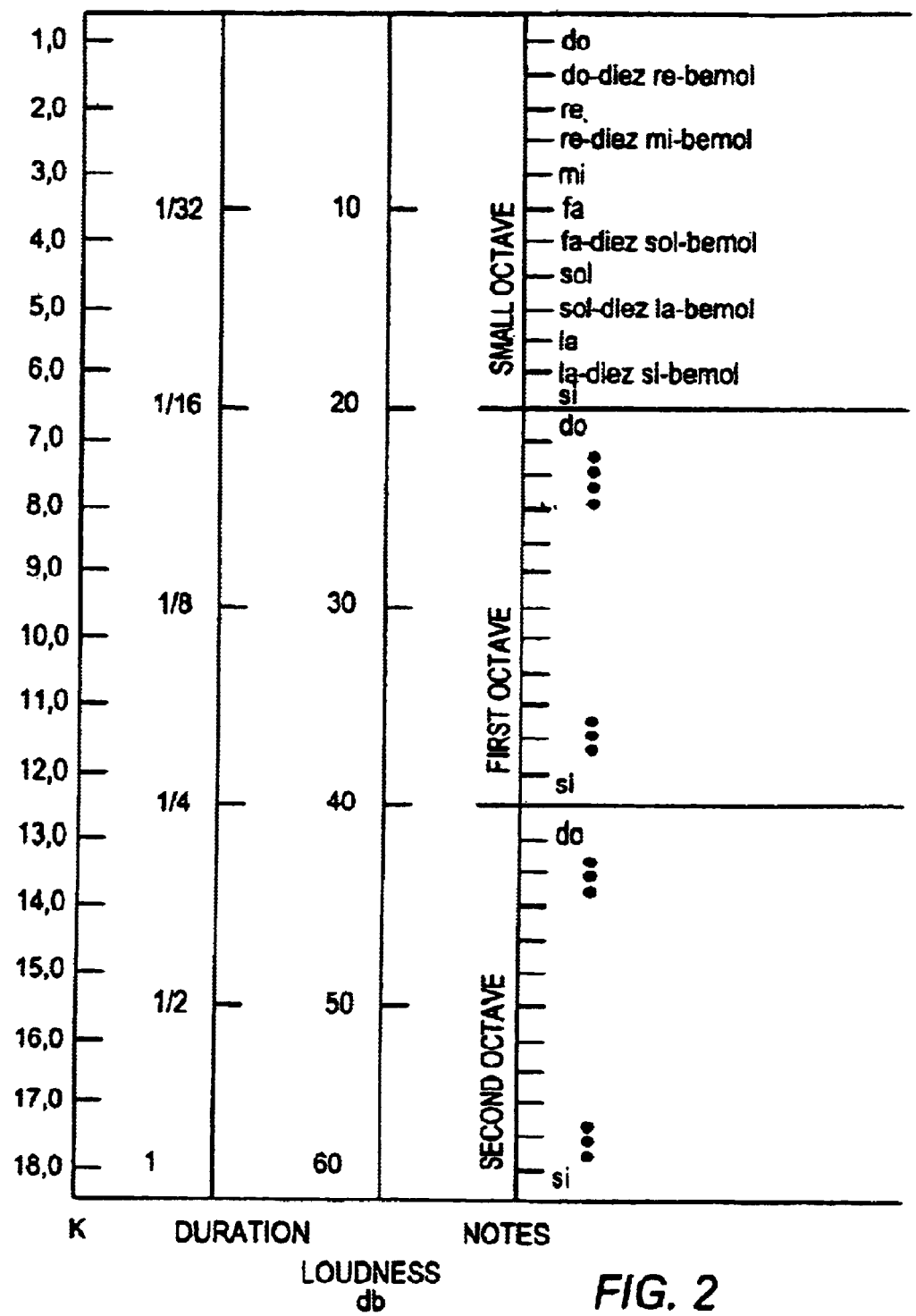
FIG. 2 shows range of musical sound parameters.

On the basis of calculation results, determined is a numerical interval between minimum ($K_1=0.5$) and maximum ($K_8=18.5$) values of generalized characteristic parameter, where drawn is a proportional range of musical sound parameters including 36 notes of three octaves (small, first and second) for piano, 8 volume gradations, and 8 duration segments (see FIG. 2), which reflects criterial relation among them. Numerical value of generalized dimensionless parameter of each spectral interval is used to determine appropriate parameters of musical sound which in the sequence appropriate to originally recorded discrete current alternation of time intervals are transformed (sonified) by means of a sound card (synthesizer) into "brain music" which is recorded on magnetic medium.

The external sound effect—music therapy according to the claimed method was successfully used for treatment of sleep disturbance in over 200 patients as follows.

Patients with sleep disturbance usually have decreased sleep duration, prolonged docinition, increased vigil time inside sleep and increased number of awakenings, increased duration of sleep surface stages (1st and 2nd stages) and decreased delta-sleep and REM duration.

To correct sleep, sleep polygram including electroencephalogram is recorded at satisfactory moment; 2nd stage, delta-sleep and REM sections according to international criteria are selected in EEG, transformed the recorded information pursuant to the claimed method into "brain music", an obtained composition is recorded in magnetic medium. In the process of correction, each patient listens to his/her "brain music" every night in bed for 15 days, which significantly improves subjective characteristic of sleep and objective sleep structure.

INDUSTRIAL APPLICABILITY

Hardware implementation of the method claimed may involve a personal computer with use of advanced electronic instrumentation—electroencephalograph, tape recorder, etc.

What is claimed is:

1. A method of influencing the body, comprising the steps of registering physical parameter biopotentials; transforming and processing of obtained data to calculate a biosignal characteristic generalized parameter; transforming the biosignal characteristic generalized parameter on the basis of detached criterial correspondence into a control signal and forming an external sound effect; implementing the external sould effect in the form of generation of musical sounds by a parametric variation tone, volume and duration thereof in criterial relation to variation of discrete current values of the characteristic generalized parameter of a frequency spectrum of the transformed biosignal; isolating from register graphic information time intervals of identical duration and transforming the time intervals using Fourier harmonic analysis into a frequency spectrum; isolating common frequent ranges ($\Delta$, $\Theta$, $\delta$, $\beta$) persuant to an internal standard $\Delta = 0.1-3.9$ Hz, $\Theta = 4.07-7.9$ Hz, $\delta = 8.0-12.9$ Hz, $\beta = 13.0-32.0$ Hz; determining a dimensionless generalized characteristic parameter for each spectral interval with respect to power spectral densities (of $\Theta$ and $\Delta$ intervals, namely:

$K_1 = P_1\Theta/P_1\beta = 15.0/30.0 = 0.5$ for 1st second
$K_2 = P_2\Theta/P_2\beta = 42.0/20.0 = 2.1$ for 2nd second
$K_3 = P_3\Theta/P_3\beta = 54.0/12.0 = 4.5$ for 3rd second
$K_4 = P_4\Theta/P_4\beta = 76.0/20.0 = 3.8$ for 4th second
$K_5 = P_5\Theta/P_5\beta = 81.4/11.0 = 7.4$ for 5th second
$K_6 = P_6\Theta/P_6\beta = 105.0/10.0 = 10.5$ for 6th second
$K_7 = P_7\Theta/P_7\beta = 78.4/93 = 0.8$ for 7th second
$K_8 = P_8\Theta/P_8\beta = 101.8/5.5 = 18.5$ for 8th second
$K_9 = P_9\Theta/P_9\beta = 51.0/8.5 = 6.0$ for 9th second
$K_{10} = P_{10}\Theta/P_{10}\beta = 135.0/6.0 = 12.5$ for 10th second wherein K is a dimensionless generalized parameter and $P\Theta$, $P\beta$ is spectral density of characteristic band power (sq.$\mu$V\sec); on the basis of calculation results determining a numerical interval between a minimum ($K_1=0.5$) and a maximum ($K_8=18.5$) values of generalized characteristic parameter, where drawn in a proportional range of musical sound parameters including 36 notes of three octaves for piano, 8 volume gradations, and 8 duration segments which reflects criterial relation among them; using a numerical value of the generalized dimensionless parameter of each spectral interval to determine appropriate parameters of musical sound, which in a sequence appropriate to original recorded alternation of time intervals are transformed by a sound card into a brain music; recording the brain music on a magnetic medium; and using an external sound effect of the brain music for a music therapy.

2. A method as defined in claim 1, further comprising determining the generalized dimensionless parameter by a ratio of power spectral densities of at least two characteristic frequency bands selected in the each spectral interval.

* * * * *